United States Patent [19]

Odell

[11] Patent Number: 4,532,212

[45] Date of Patent: Jul. 30, 1985

[54] PROCESS FOR THE DISSOLUTION OF PEPTIDES IN NON-AQUEOUS AND MIXED NON-AQUEOUS/AQUEOUS SYSTEMS

[75] Inventor: Barbara Odell, Landor Court, England

[73] Assignee: Shell Oil Company, Houston, Tex.

[21] Appl. No.: 624,570

[22] Filed: Jun. 26, 1984

[30] Foreign Application Priority Data

Jun. 29, 1983 [GB] United Kingdom ............... 8317697

[51] Int. Cl.$^3$ .................... C12H 9/18; C12H 9/20; C12H 9/50; C07G 7/00
[52] U.S. Cl. ................... 435/197; 260/112 R; 260/112 B; 260/112.5 R; 260/112.7; 260/113; 260/121; 260/122; 435/198; 435/213; 435/219
[58] Field of Search ............ 260/112 R, 112 B, 115, 260/113, 112.7, 121, 122; 435/197, 198, 219, 213

[56] References Cited

U.S. PATENT DOCUMENTS 4,156,683  5/1979  Lehn .................................. 260/338

OTHER PUBLICATIONS

H. Tsukube, "Active and Passive Transport of Amino-Acid and Oligopeptide Derivatives by Artificial Ionophore—K+ Complexes", J. Che. Soc. Perkin Trans., vol. I, (1982), pp. 2359–2363.
Synthesis, vol. 82, No. 5, pp. 412–414, Lejczak et al.
U. Olsher, "Solvation Properties of Natural and Synthetic Ionophores", Biophys. J., vol. 40, (Oct. 1982), pp. 61–68.

Primary Examiner—Howard E. Schain

[57] ABSTRACT

Process for the dissolution of peptides and proteins in non-aqueous and mixed non-aqueous/aqueous solvents using crown ethers, solutions thereby obtained and their use. Purification of proteins and/or enzymes, modification and optimisation of the activity of enzymes. Use of peptide-crown ether complexes as membrane materials, use of enzyme-crown ether complexes as detergents.

13 Claims, No Drawings

PROCESS FOR THE DISSOLUTION OF PEPTIDES IN NON-AQUEOUS AND MIXED NON-AQUEOUS/AQUEOUS SYSTEMS

The present invention relates to a process for the dissolution of peptides in non-aqueous and mixed non-aqueous/aqueous solvents.

Peptides are biological or synthetic compounds which consist of two or more amino acids linked together by peptide bonds which are combinations of a carbonyl and an amino group. In this patent application the term peptide will refer to oligopeptides containing four or more amino acids, to the higher polypeptides and to proteins, while the term peptides further encompasses derivatives of peptides like enzymes and related substrates i.e. compounds which contain oligopeptide and/or polypeptide chains.

Applicants have tried to dissolve peptides in non-aqueous solvents like methanol and ethanol but in most cases no positive result was obtained. However it has now been found that those peptides can be successfully dissolved in non-aqueous and mixed non-aqueous/aqueous solvents if crown-ethers are present in certain concentrations.

In this application the term crown-ether means a highly selective complexing agent which can form complexes with metal ions like alkali and alkaline earth cations via electrostatic interactions. From J. Chem. Soc. Perkin Trans. I, 1982 pp. 2359–2363 several types of crown-ethers are known such as the cyclic crown-ether, the diaza-crown-ether, the non-cyclic crown-ether and the cryptand all being polyethers or polyethers in which one or more of the oxygen atoms have been substituted by a nitrogen atom and/or another heteroatom.

The fact that crown-ethers appear to be able to get even large protein molecules into solution in a solvent system comprising non-aqueous and/or mixed non-aqueous/aqueous solvents, opens the possibility of a wide range of applications in the first expanding field of biotechnology.

Therefore the present invention provides a process for the dissolution of peptides in a non-aqueous and/or mixed non-aqueous/aqueous medium in the presence of a crown-ether or a mixture of crown-ethers in a molar or average molar crown-ether/peptide ratio which is in the range of 10–100,000. Preferably the molar or average molar crown-ether/peptide ratio is in the range of 50–30,000.

Preferably the non-aqueous medium is a hydrogen bonding solvent. Furthermore the non-aqueous medium has preferably a dielectric constant which is in the range of 20–100 at 25° C. Preferred solvents with an appropriate dielectric constant are selected from the group consisting of methanol, ethanol and dimethylsulphoxide. The non-aqueous or mixed non-aqueous/aqueous medium may suitably comprise in addition to the above hydrogen bonding solvents, non-hydrogen bonding solvents such as for example ethyl acetate, acetone and chloroform.

Suitable crown-ethers and related compounds such as crown-related macrocycles, cryptands and acyclic multidentates which should all be considered to be within the scope of the invention may be selected from the group of macromolecular ligands which have been described in Chemical Reviews 1979 vol. 79 No. 5 pp. 389–445, (1979 American Chemical Society) and from the macrocyclic compounds which have been described in U.S. 4156683. Crown-ethers which are preferably used in the present process are selected from the group consisting of 12-crown-4, 15-crown-5, 18-crown-6, 21-crown-7, dibenzo-18-crown-6 and cryptand [2.2.2]. Peptides which easily dissolve in non-aqueous organic solvents in the presence of crown-ethers and which are therefore preferred are selected from the groups consisting of myoglobin (whale muscle), bovine-serumalbumin, bovine insulin, cytochrome c (horse heart), cholesterol esterase (microbial), papain, lipase (Rhizopus arrhizus), acetyl esterase and histones.

It appeared that the best results are obtained when the peptides are substantially metal salt-free. Therefore it is preferred that the peptides are substantially metal salt-free. The present invention further relates to non-aqueous and mixed non-aqueous/aqueous solutions comprising one or more peptide crown-ether complexes which solutions have been prepared using the present process.

Dissolution of peptides in non-aqueous and mixed non-aqueous/aqueous media may preferably be effected by chemically linking crownethers to the peptides and this technique should also be considered to be within the scope of the present invention. As will be appreciated the present invention offers a whole range of possible applications in the field of biotechnology, especially for those applications for which it is essential that peptides and especially proteins can be dissolved in non-aqueous and mixed non-aqueous/aqueous solutions. For example protein and enzyme purification and separation can be more successfully carried out if the protein or enzyme can be dissolved in organic solvents or in aqueous organic solvent mixtures which makes it possible that fractional precipitation and/or crystallisation, chromatographic and electrophoretic techniques can be applied.

Other potential applications are to be found, for example, in methods for the immobilisation of proteins and enzymes which comprises the use of polymeric and polymer-bond crown ethers, in the modification and optimisation of the activities of enzymes in organic solvents and in aqueous organic solvent mixtures, and in the retrieval of enzyme activity from solvent mixtures containing enzymes. Furthermore the peptide-crown-ether complexes may preferably be utilised as membrane materials while enzyme-crownether complexes could preferably be applied as detergents.

The present invention will now further be described with reference to the following Examples.

EXAMPLE I

Dissolution of Peptides

In the table examples are given of peptides which dissolve in methanol, ethanol or dimethylsulphoxide in the presence of certain crown ethers.

TABLE 1 (a)

Small Peptides and Proteins which
Dissolve in Organic Solvents using Crown Ethers and Cryptands

| Peptide/protein | Number of amino acid residues | Solvent | Molar ratio of peptide/protein:Crown ether | | | | |
| --- | --- | --- | --- | --- | --- | --- | --- |
| | | | 12-Crown-4 | 15-Crown-5 | 18-Crown-6 | 21-Crown-7 | Cryptand [2.2.2.] |
| Bovine insulin (A) | 21 | MeOH | | | 1:75 | | |
| (B) | 30 | MeOH | | | 1:102 | | |
| (A-B) | 51 | MeOH | | in* | 1:1207 | | 1.120 |
| Cytochrome c Horse heart | 104 | MeOH EtOH DMSO | 1:1220 | 1:1200 | 1:127–300 1:2000 1:1900 | 1:798 | 1:120 |
| Bovine serum albumin (BSA) | 513 | MeOH | in* | | 1:426 | 1:16130 | 1:309 |
| Myoglobin (whale skeletal muscle) | 153 | MeOH | | in* | 1:2109 | | 1:212 |
| α-chymotrypsin (bovine pancreas) | 245 | MeOH | | | in* | | in* |
| Papain | 198 | MeOH | | | $1:1 \times 10^4$ | | |
| Cholesterol esterase | 646 | MeOH | | | $1:1 \times 10^4$ | | |
| Lysozyme (egg white) | 129 | MeOH | | | 1:150 | | |
| Histone III-S (calf thymus) | >100 | MeOH | | | $1:1.75^b$ | | |
| Histone VIII-S (calf thymus) | >100 | MeOH | | | in* | | |

*in = insoluble (independent of crown ether)
[b] weight ratio of protein:crown ether
[a] Protein concentration was in the range 0.05–0.8 mM depending on protein (i.e. cytochrome c, concentration was 0.8 mM, whereas, myoglobin concentrtion was 0.1 mM). In a typical experiment, small portions of CE (ca 2.0 mg, $7.6 \times 10^{-3}$ mmoles) were added to a suspension of protein/peptide (5 mg) in methanol (2 ml) at 4–25° C. with stirring until the suspension dissolved.

EXAMPLE II

The Use of Crown Ethers/Cryptands in Protein Separation, Purification (a) Separation of Cytochrome c from α-Chymotrypsin Cytochrome c readily dissolves in methanol with relatively low concentrations of crown ether, while α-chymotrypsin is totally insoluble. Thus mixtures of cytochrome c and α-chymotrypsin (10 mg each, $8.1 \times 10^{-4}$ and $4 \times 10^{-4}$ m.mole, respectively) were treated with 18-crown-6 (28 mg, 0.11 m.mole) in methanol (2 ml). The red solution was filtered from undissolved protein (α-chymotrypsin) and dialysed against water, then buffer (Tris, pH 7.5, 0.10 M). Both filtrate and filtered protein fractions were examined using isoelectric focusing in order to establish the purity of the separations (results shown in Table 2).

(b) Separation of Cytochrome c from a Mixture of Cytochrome c, BSA and α-Chymotrypsin Cytochrome c dissolves in methanol at a lower crown ether concentration than BSA whilst α-chymotrypsin is insoluble. Mixtures of cytochrome c, BSA and α-chymotrypsin (10 mg each, $8.1 \times 10^{-4}$, $1.4 \times 10^{-4}$ and $4 \times 10^{-4}$ m.mole respectively) were treated with 18-crown-6 (50 mg, 0.19 m.mole) in methanol (2 ml) and the resulting red solution was filtered and then dialysed against water then buffer (Tris, pH 7.5, 0.01 M) to remove crown ether and methanol. Both soluble and insoluble fractions were examined using iso-electric focusing (results shown in Table 2).

TABLE 2

Protein Separations using Crown Ether/Methanol Solutions

| Protein mixtures | Iso-electric focusing results | | Protein estimn.* (Lowry) | |
| --- | --- | --- | --- | --- |
| | (a) Soluble fraction | (b) Insoluble fraction | (a) Soluble fraction | (b) Insoluble fraction |
| { cytochrome c<br>α-chymotrypsin | cytochrome c<br>($pH_I$ 9.35) | α-chymotrypsin<br>($pH_I$ 8.7–7.4) | 55% cytochrome c | 32% α-chymotrypsin |
| { cytochrome c<br>BSA<br>α-chymotrypsin | cytochrome c<br>($pH_I$ 9.35) | BSA ($pH_I$ 5.5–6.0)<br>α-chymotrypsin (trace, $pH_I$ 8.7–74) | 51% cytochrome c | 28% BSA |

*Protein estimations based on 10 mg of each protein present at start of experiment - possible protein losses could be attributed to denaturation and the fact that protein determinations were inaccurate due to traces of crown ether which interfered with the absorbance measurements (Lowry method).

The filtrates in both cases only contained one component, cytochrome c. The insoluble fractions contained the less soluble proteins, higher yields of which could be obtained if $(NH_4)_2SO_4$ is used as an additive at 0°–4° C.

EXAMPLE III

The Use of Crown Ethers in Protein Crystallisation

Proteins such as cytochrome c and bovine insulin containing crown ether and $(NH_4)_2SO_4$ as stabilising agent could be each obtained as crystalline composites from methanol solutions. For example, cytochrome c (20 mg, $1.6 \times 10^{-3}$ m.mole) was treated with a methanol (10 ml) solution containing 18-crown-6 (55 mg, 0.21 m.mole) and $(NH_4)_2SO_4$ (50 mg 0.38 m.mole). The solubilised protein solutions were stored at 4° C. within an outer tube containing ethyl acetate as precipitating co-solvent. After 1 week, crystalline material formed, which could be filtered, and was found to be water-soluble. Protein analysis indicated the solid material contained 20% by weight protein. Circular dichroism (CD) and UV/visible spectroscopy indicated intact protein present. Crystalline material containing bovine insulin could be obtained from a solution comprising bovine insulin (5 mg, $8.6 \times 10^{-4}$ m.mole), 18-crown-6 (300 mg, 1.14 m.mole) and $(NH_4)_2SO_4$ (300 mg, 2.3 m.mole) in methanol (5 ml) and ethyl acetate as precipitating solvent. The CD spectrum was similar to that of pretreated protein (negative band at 225–200 nm).

EXAMPLE IV

The Use of Polymer-Bound Crown Ethers for Protein and Enzyme Immobilisation

A cryptand bound polymeric material, (KRYPTOFIX 221B polymer), obtained from Merck-Schuchardt and comprising an aryl-cryptand [2.2.1] attached to a MERRIFIELD polymer can be used as an immobilisation support material for proteins (e.g. cytochrome c) and enzymes (e.g. α-chymotrypsin). Proteins (enzymes) could be immobilised under mild conditions (requiring no further chemical modification) by simply suspending the protein (enzyme) ca. $0.4-4 \times 10^{-3}$ m.mole with 500 mg of the polymeric material in buffer for 16–200 h at 4° C. The immobilised enzyme material was filtered off and washed thoroughly (ca. 30 ml buffer) prior to assay. In the case of α-chymotrypsin, 40 mg of protein and 500 mg of polymer were suspended in 0.001 N HCl (ml) for 16 h at 4° C. In the case of cytochrome c, 5 mg $0.4 \times 10^{-3}$ m.mole of protein and 15 mg of support were suspended in Tris buffer (0.01 M, pH 7.5), 1 ml for 200 h at 4° C. The enzyme activities and protein loadings are summarised in Table 3 together with results obtained for MERRIFIELD polymer without cryptand.

to separate the enzyme from complexant and solvent, enzyme activity can be retrieved. It may be necessary to also employ a stabilising agent (e.g. $(NH_4)_2SO_4$) which does not interfere with the complexing ability of the crown ethers but protects the protein against irreversible denaturation. It is believed that temperature is important and should be kept below 4° C. during manipulations.

Two enzymes have been examined:

Cholesterol esterase—which is soluble in organic solvent/crown ether mixtures.

α-Chymotrypsin—which is insoluble in methanol crown ether mixture, but if a concentrated solution of the enzyme is first prepared in water, then methanol containing crown ether can be added without protein precipitation (ca. methanol:water, 85:15).

(a) Method for Retrieving Cholesterol Esterase Activity from an Organic Solvent/Methanol Mixture using Crown Ethers In a typical experiment, cholesterol esterase (Boehringer Mannheim) from micro-organism sterol-ester acylhydrolase, suspension in $(NH_4)_2SO_4$, ca. 0.4–0.6 mg, 10–15 U)* was dissolved in a methanol solution (2–6 ml) containing 18-crown-6 (0.1–0.3 g, 0.4–1.1 m.mole) at 0°–4° C. The mixture was dialysed against water (16 h) and then eluted through a short Sephadex G25 column (void volume 8 ml) with sodium phosphate buffer (pH 6.2, 0.1 M). Protein estimations were determined by Lowry method[1]. Eluted samples were assayed for enzyme activity using cetyl alcohol (1.72 mM) and oleic acid (2.37 mM) as substrates in phosphate buffer (pH 6.5, 0.05 M, at 37° C.) containing sodium taurocholate and 3.3% isopropanol. The product of esterase activity, cetyl oleate was monitored by extraction (0.5 ml aliquots from 9 ml enzyme mixtures) into chloroform (2 ml) and detection by gas-liquid chromatography

TABLE 3

Data for the Immobilisation of α-Chymotrypsin and Cytochrome c onto KRYPTOFIX 221B Polymer

| Protein/enzyme | Polymeric material | mg of protein on support | loading** | Enzyme* initial rate μmol/min | Specific* activity μmol/min/mg |
|---|---|---|---|---|---|
| α-Chymotrypsin 40 mg $1.6 \times 10^{-3}$ m.mole | KRYPTOFIX 221B 500 mg | 17.7 | 3.5 | 30 | 1.7 |
| α-Chymotrypsin 100 mg $4 \times 10^{-3}$ m.mole | KRYPTOFIX 221B 132 mg | 5.4 | 4.1 | 30 | 5.6 |
| α-Chymotrypsin 0.05 mg $2 \times 10^{-3}$ μ.mole | Free enzyme | 0.05 | — | 15 | 300 |
| α-Chymotrypsin 40 mg $1.6 \times 10^{-3}$ m.mole | MERRIFIELD polymer (unmodified) 500 mg | 24 | 4.8 | 7.5 | 0.3 |
| Cytochrome c 5 mg $0.4 \times 10^{-3}$ m.mole | KRYPTOFIX 221B 15 mg | 1.58 | 10.5 | — | not measured |

**Loading = grams of protein adsorbed onto support divided by grams of support × 100.
*Enzyme assay was carried out using pH-stat titrimetric methods involving N—acetyl-tyrosine ethyl ester (ATEE) at an initial concentration of 0.01 M, as substrate at 26° C. in Tris/CaCl₂ buffer (pH 7.75, 0.01 M), according to Methods in Enzymology XIX, 73, 1970. Edited by G. E. Perlmann and L. Lorand, Academic Press.
α-Chymotrypsin from bovine pancreas, 3 × crystallised (Sigma Chemical Co.). Cytochrome c from horse heart (Type III, from Sigma Chemical Co.). The cryptand/polymer immobilised enzyme (α-chymotrypsin) showed an operational half-life of 56 days at 20° C.

EXAMPLE V

The Retrieval of Enzyme Activity from Non-Aqueous and Mixed Non-Aqueous/Aqueous Media using Crown Ethers Reversibility of the crown ether/protein complexation phenomenon can be demonstrated by recovering enzyme activity from organic media into aqueous solution. By using simple and gentle manipulative techniques such as dialysis and gel filtration, which are used (carried out on a Varian 3700 gas chromatograph with flame ionisation detector using a 2 ft, 3% SE 30 packed column of internal diameter 2 mm; carrier gas nitrogen at 30 ml/min, programmed for 100°–260° at 10°/min). One cetyl oleate unit of cholesterol esterase activity was defined as the amount of enzyme (in mg) required to synthesise 1 μmol of cetyl oleate/min under the conditions of the assay. The results of enzyme activities are summarised in Table 4.

* U=Unit of specific activity of the enzyme on cholesterol oleate as substrate as defined in the Boehringer Mannheim Catalogue 1984.
[1] H. O. Lowry, N. H. Rosenbrough, A. L. Farr and R. J. Randell, J. Biol. Chem., 193, 1951, 265.

TABLE 4

Retrieval of Cholesterol Esterase Activity from Methanol/Crown Ether Solutions into Aqueous Phase

| Enzyme system | Method of retrieval | % Protein recovered | Initial rate $\mu$mol/min | Specific activity of remaining protein $\mu$mol/min/mg |
|---|---|---|---|---|
| Aqueous | | | | |
| Control-cholesterol esterase in buffer | gel filtration | 85.8 | 1.32 | 6.4 |
| Control-cholesterol ester in buffer | dialysis + gel filtration | 75 | 1.0 | 8.89 |
| Non-aqueous | | | | |
| Cholesterol esterase dissolved in MeOH/18-crown-6 | gel filtration* dialysis + gel filtration | 36 39 | — 0.43 | — 7.25 |

*Initial rate not recorded, but 65.4% esterification was achieved after 16 h.

(b) Method for Retrieving -60 -Chymotrypsin Activity from Mixed Non-Aqueous/Aqueous Solvent System using Crown Ethers A procedure is carried out, whereby concentrated solutions of α-chymotrypsin (bovine pancreas, Sigma Chemical Company, ~1.2 mM in 0.001 MHCl, 0.75 ml) are carefully (slow addition) treated at 40° C. with solutions of methanol 5 ml containing 18-crown-6 (0.9 M) and, in some cases, enzyme inhibitor, indole (0.034 M) to protect the active site. The enzyme mixtures are then purified by repeated dialysis (ca. 5 x against 0.001 NCl), followed by gel filtration using eluant 0.001 NCl and Sephadex G25 column of dimensions 3×40 cm).

Enzymes samples and corresponding controls are assayed for activity using a spectrophotometric method employing substrate N-benzoyl-L-tyrosine* ethyl ester (BTEE) prepared in 0.1 M Tris-HCl buffer (pH 7.8, containing $CaCl_2$ 0.1 M). Molarity of active sites are determined using active site titrant, 2-hydroxy-α-toluene sulphonic acid sultone*. One BTEE unit of α-chymotrypsin activity was defined on the amount necessary to hydrolyse one $\mu$mole of BTEE per minute under the conditions of the assay.

* Methods in Enzymology, Vol. XIX, 1970, Edited by G. E. Pearlmann and L. Lorand, Academic Press.

The results of α-chymotrypsin activity after dissolution in aqueous methanol are summarised in Table 5.

TABLE 5

Results for α-Chymotrypsin Activity from Aqueous-Methanolic Solutions Containing 18-crown-6 using BTEE Substrate at 30° C.

| Enzyme system | Solvent system | Inhibitor indole | % Protein recovered | Molarity of active sites | Specific activity remaining protein $\mu$mol/min/mg |
|---|---|---|---|---|---|
| Control (α-chymotrypsin (no crown ether) | 0.001 M HCl 5.75 ml | 0.034 M | 98% | 85% | 62 |
| Control (α-chymotrypsin) (no crown ether, ppt) | MeOH 0.001 M HCl 5 ml 0.75 ml | 0.034 M | 20–30% | — | 20–28 |
| α-chymotrypsin + 18-crown-6 0.9 M | MeOH 0.001 M HCl 5 ml 0.75 ml | 0.034 M | 50–95% | 50–70% | 30–56 |
| α-chymotrypsin + 18-crown-6 0.9 M | EtOH 0.001 M HCl 1.6 ml 0.5 ml | 0.034 M | 80–100% | 47% | 35 |
| α-chymotrypsin + 18-crown-6 0.9 M | MeOH 0.001 M HCl 5 ml 0.75 ml | — | 57% | 57% | 63 |

What is claimed is:

1. A process for the dissolution of one or more peptides containing four or more amino acids in a non-aqueous solvent or a mixed non-aqueous/aqueous solvent which comprises dissolving the peptides in a nonaqueous or mixed nonaqueous/aqueous solvent comprising as a solubilizing agent one or more crown-ether compounds in a molar ratio of crown-ether compounds to peptides in the range of 10 to 100,000.

2. A process according to claim 1, in which the molar ratio of crown-ether compounds to peptides is in the range from about 50 to 30,000.

3. A process in accordance with claim 2, wherein the nonaqueous solvent or the nonaqueous component of the mixed solvent is a hydrogen-bonding solvent.

4. A process in accordance with claim 3, wherein the one or more crown-ether compounds are selected from the group consisting of 12-crown-4, 21-crown-7, 18-crown-6, 15-crown-5, [2.2.2.]-cryptate, dibenzo-18-crown-6, and mixture thereof.

5. A process is accordance with claim 1, wherein the one or more crown-ether compounds are selected from the group consisting of 12-crown-4, 21-crown-7, 18-crown-6, 15-crown-6, [2.2.2.]-cryptate, dibenzo-18-crown-6, and mixture thereof.

6. A process in accordance with claim 1, wherein the peptide is selected from the group consisting of myoglobin, bovine serum albumin, bovine insulin, cytochrome c, cholesterol esterase, papain, lipase, acetyl esterase, and histones.

7. A process in accordance with claim 6, in which the peptide is substantially metal salt free.

8. A process in accordance with claim 2, wherein the peptide is selected from the group consisting of myoglobin, bovine serum albumin, bovine insulin, cytochrome c, cholesterol esterase, papain, lipase, acetyl esterase, and histones.

9. A process in accordance with claim 8, in which the peptide is substantially metal salt free.

10. A process in accordance with claim 4, wherein the peptide is selected from the group consisting of myoglobin, bovine serum albumin, bovine insulin, cytochrome c, cholesterol esterase, papain, lipase, acetyl esterase, and histones.

11. A process in accordance with claim 10, in which the peptide is substantially metal salt free.

12. A process in accordance with claim 5, wherein the peptide is selected from the group consisting of myoglobin, bovine serum albumin, bovine insulin, cytochrome c, cholesterol esterase, papain, lipase, acetyl esterase, and histones.

13. A process in accordance with claim 12, in which the peptide is substantially metal salt free.

* * * * *